US006818396B1

(12) United States Patent
Bloch et al.

(10) Patent No.: US 6,818,396 B1
(45) Date of Patent: Nov. 16, 2004

(54) PROCESS FOR DETERMINATION OF THE ACTIVITY OF A SUBSTANCE USING AN IN VITRO FUNCTIONAL TEST

(75) Inventors: Jean François Bloch, Nimes (FR); Daniel Dupret, Calvisson (FR); Fabrice Lefevre, Nimes (FR); Sandrine Dautel, Nimes (FR); Jean-Michel Masson, Toulouse (FR)

(73) Assignee: Proteus S.A., Nimes (FR)

( * ) Notice: Subject to any disclaimer, the term of this patent is extended or adjusted under 35 U.S.C. 154(b) by 117 days.

(21) Appl. No.: 09/722,587

(22) Filed: Nov. 28, 2000

(51) Int. Cl.⁷ .................................................. C12Q 1/68
(52) U.S. Cl. .......................... 435/6; 435/183; 435/91.1; 435/91.2
(58) Field of Search .......................... 435/6, 183, 91.1, 435/91.2; 436/89; 536/23.1; 424/88

(56) References Cited

U.S. PATENT DOCUMENTS

| | | | |
|---|---|---|---|
| 4,557,862 A | | 12/1985 | Mangel et al. |
| 5,360,714 A | * | 11/1994 | Seeger .......................... 435/5 |
| 5,763,198 A | | 6/1998 | Hirth et al. |
| 5,767,233 A | * | 6/1998 | Zhang et al. ............... 530/326 |

FOREIGN PATENT DOCUMENTS

| | | |
|---|---|---|
| EP | 518557 | 12/1992 |
| EP | 864656 | 9/1998 |
| GB | 2276621 | 10/1994 |
| JP | 07184648 | 7/1995 |
| WO | WO 92/07949 | 5/1992 |
| WO | WO 94/058120 | 3/1994 |
| WO | WO 94/24303 | 10/1994 |
| WO | WO 95/09925 | 4/1995 |
| WO | WO 96/08580 | 3/1996 |

OTHER PUBLICATIONS

1991 GIBCO BRL Supplement and Price List, (1991), p. 736.*
Fritsch et al. Clining and characterization of a 77–kDa o estrogen receptor isolated from a human breast cancer cell line. British J. of Cancer vol. 75(1):17–27, 1997.*
Fussenegger et al., "Regulated Multicistronic Expression Technology for Mammalian Metabolic Engineering", *Cytotechnology*, NL, Kluwer Academic Publishers, Dordrecht, vol. 28, No. 28, pp. 111–125–25 (1998).
Ohuchi et al., "In Vitro Method for the Generation of Protein Libraries Using PCR Amplification of a Single DNA Molecule and Coupled Transcription/Translation", *Nucleic Acids Research*, vol. 26, No. 19, pp. 4339–4346 (1998).
Resto et al., "Amplification of Protein Expression in a Cell Free System", *Nucleic Acids Research*, vol. 20, No. 22, pp. 5979–5983 (1992).
Uchida, et al., "Selection of Antisense Oligodeoxyribonucleotides that Inhibit VEGF/VPF Expression in a Cell–Free System", *Antisense Research and Development*, vol. 5, pp. 87–88 (1995).

* cited by examiner

*Primary Examiner*—James Ketter
(74) *Attorney, Agent, or Firm*—Hunton & Williams LLP

(57) ABSTRACT

The invention concerns a method for determining the activity of a substance using a functional test, characterized in that it consists in detecting and/or measuring the variation of a known function corresponding to one or several proteins produced in vitro in the presence and in the absence of said substances or to the substance in the presence or in the absence of one or several proteins produces in vitro.

24 Claims, 8 Drawing Sheets

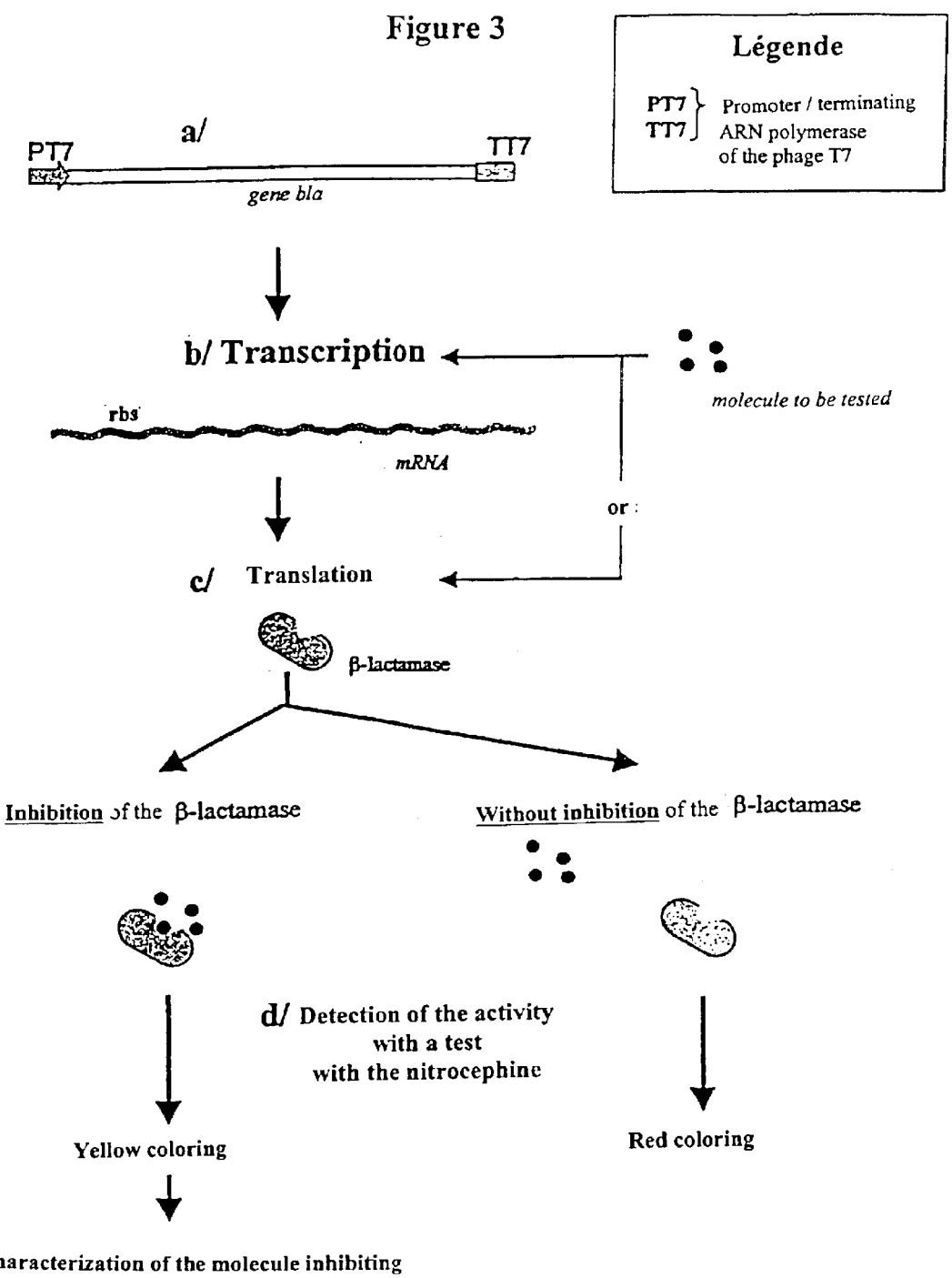

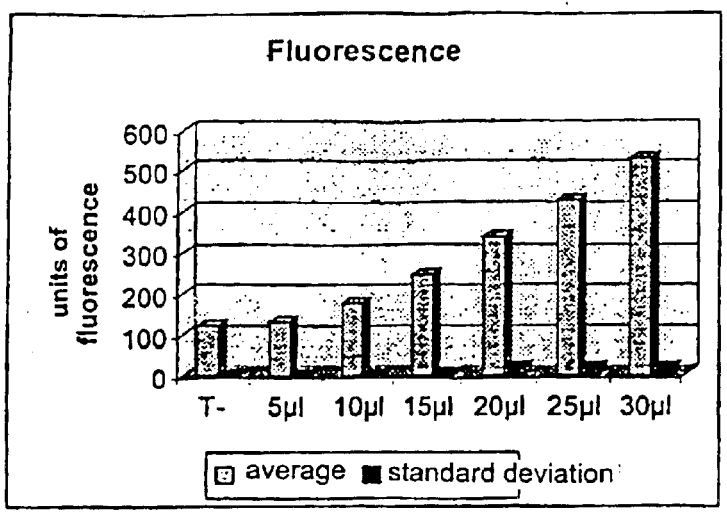
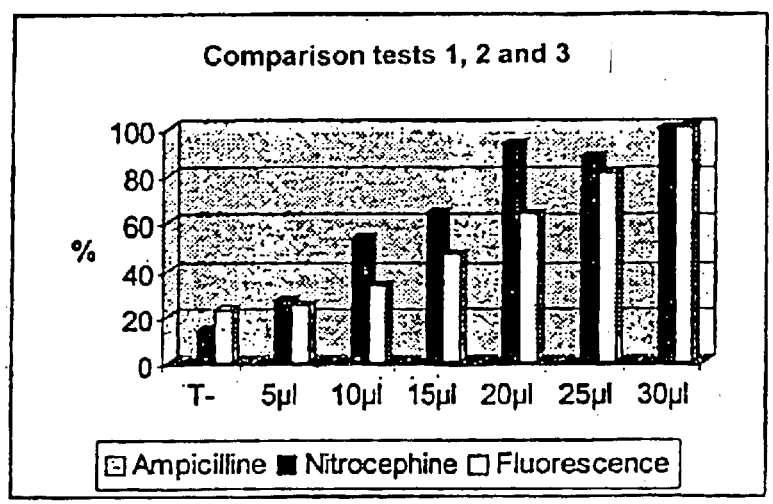
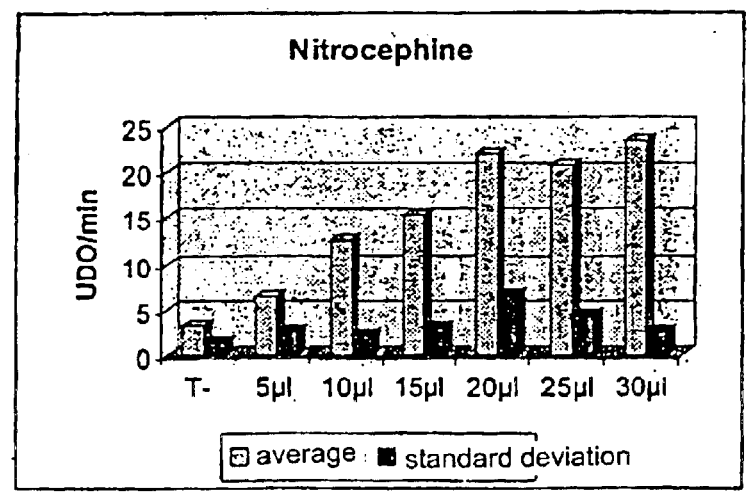
Figures 4 - 5 - 6 : Comparison of the sensitivity and the reproducibility of several methods of detection of a function.

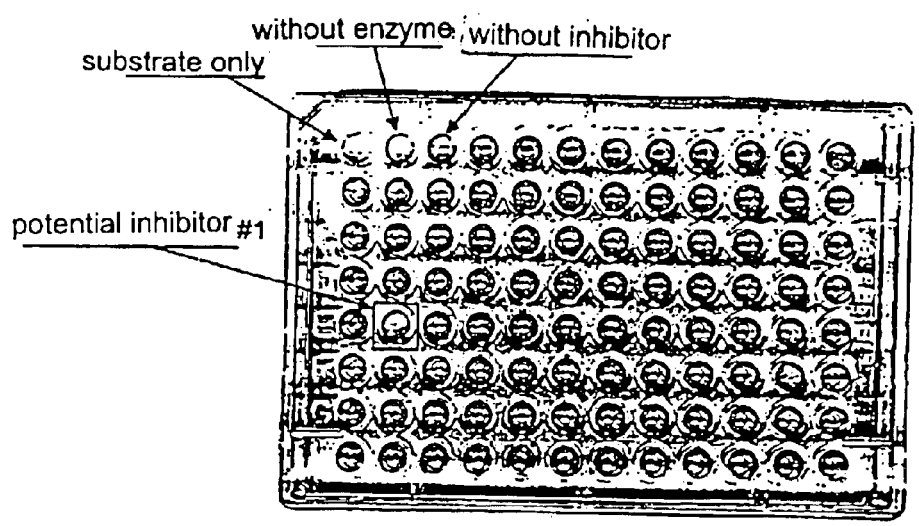
Figure 7: Effect of various substances (final 0.4μM) on the variation of activity of beta-lactamase TEM-1

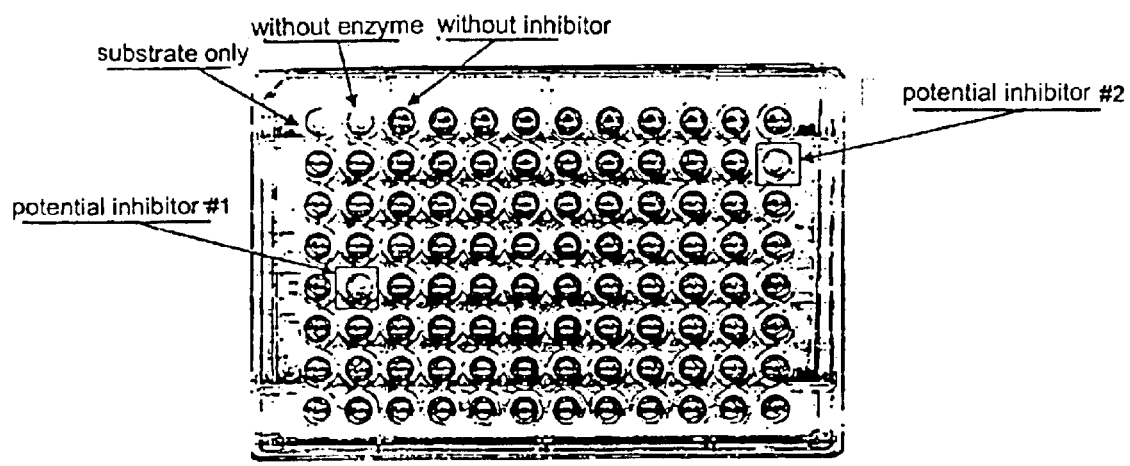
Figure 8 : Effect of various substances (final 21.5µM) on the variation of activity of the beta-lactamase TEM-1

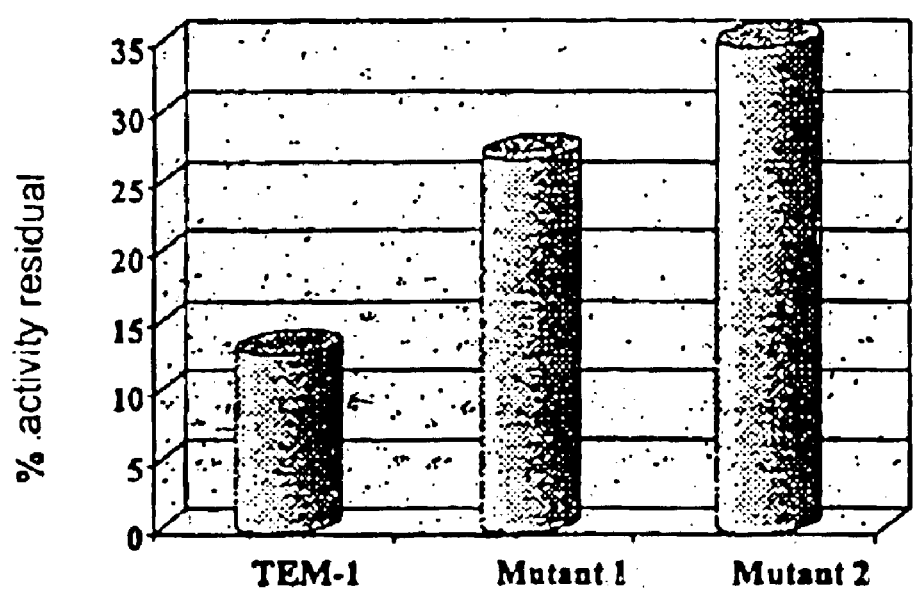
Figure 9 : Characterization of resistance to an inhibitor

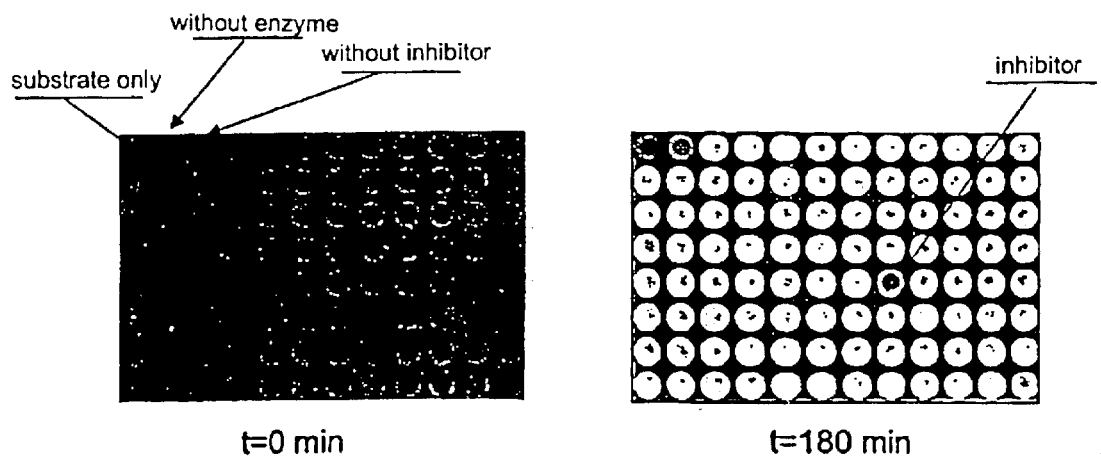
Figure 10 : Effect of various substances (final 2.5µM) on the variation of activity of the protease of the HIV virus

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

Ser Gln Asn Tyr Pro Ile Val Gln
1               5

PROCESS FOR DETERMINATION OF THE ACTIVITY OF A SUBSTANCE USING AN IN VITRO FUNCTIONAL TEST

CROSS-REFERENCED APPLICATIONS

This application is a continuation application of PCT Application No. PCT/FR99/03062, filed Aug. 12, 1999, which claims the benefit of French Application No. 98/15488, filed Aug. 12, 1998.

FIELD OF INVENTION

The present invention relates to the filed of research of substances capable of modifying a function corresponding to a protein or a collection of proteins implicated in a biological process. This type of work, also designated screening, today constitutes an empirical mode of research but particularly for forming new substances, used in numerous laboratories. Among the numerous fields of application of these screening strategies, there can be cited the following examples:

Pharmaceutical laboratories set up libraries of molecules, and research those capable of inhibiting or of slowing down the activity of enzymes implicated in the development of genetic or infectious bacterial or viral diseases.

Following the intensive use of antibiotics, the speed of the appearance of new resistances is currently more rapid than that of the discovery of new antibiotics. Certain hospital laboratories therefore are looking for, always starting from banks of very specific molecules, new antibiotics or new beta-lactamase inhibitors.

Work is equally being carried out to find inhibitors of microorganism multiplication implicated in the biological corrosion of pipes or of containers used in industrial processes.

DETAILED DESCRIPTION OF PREFERRED EMBODIMENTS

The present invention has for its object a process for the determination of the activity in vitro of one or several substances using a functional test consisting of detecting and/or measuring a variation of at least one known function corresponding either to one or several proteins produced in vitro in the presence or absence of said substance, or of the substance in the presence or in the absence of proteins produced in vitro. The process of the invention will therefore be designated hereinafter, screening process.

Said known function preferably corresponds to proteins expressed in vitro also called target proteins. The process of the invention therefore aims to determine the activity of the substance tested based on a known function corresponding to one or several protein(s) produced in vitro.

However, in another embodiment of the process of the invention, the known function corresponds to the substance(s) tested. In this case, the process of the invention permits determining if the known activity of this substance is modified by one or several protein product(s) in vitro.

By function is understood the activity of one or several specific proteins still called target proteins of at least one organisms or of at least a process, and that it is detected and/or quantified according to the present invention by the by means of a functional test. Preferably, the target protein is an enzyme. This enzyme can correspond among other things to reverse transcriptase or to the aspartic acid proteinase of the Aids virus, to the *Mycobacterium tuberculosis* RecA intein, to an antibiotic resistance protein, or also to a collection of enzymes implicated in a metabolic pathway.

By known function is understood the function that is analyzed according to the process of the invention and which can be detected and/or measured by a functional test.

In a particular case of the process of the invention, function is understood as the activity of one or more substances that are detected and/or measured by a functional test.

Variation of function is understood as the difference of the activity of the measured function in the presence or absence of substance. In a second embodiment of the process of the invention, the variation in function corresponds to the activity difference of the substance in the presence of or in the absence of protein expressed in vitro.

The functional test can make use of one or multiple reporter molecules. The reporter molecule can correspond to any molecule capable of directly or indirectly revealing the activity of one or multiple target proteins, and can include a nucleic acid molecule, a protein, a peptide, such as an antibody or a mixture of specific antibodies capable of revealing the activity of a target protein, or such as a substrate or a cascade of substrates, of which one is that of a target protein.

The function can correspond to an enzymatic activity or to an affinity. In the scope of the demonstration of a variation of function corresponding to an enzymatic activity, any type of specific functional test can be contemplated by a person skilled in the art to demonstrate this variation. A person skilled in the art for example can make reference to works such as Methods In Enzymology or Annual Review of Biochemistry, in which a large number of enzyme measuring and substrate preparation methods have been described. In the case of the demonstration of a variation of function corresponding to the affinity for example of an antigen for an antibody, of a protein for DNA, of a receptor for a ligand etc . . . . The demonstration of a variation of function can be carried out for example by tests such as labeled ligand fixation by an isotope or by an enzyme or by a fluorophore, by an immunological detection using antibodies labeled by a metal or by an enzyme or by a fluorophore.

By organism is understood any type of organism or microorganism, such as viruses, bacteria, algae, fungi, or any product containing synthetic or natural nucleic acids permitting the expression of one or more proteins advantageously coding for a function.

By process is understood the development of a disease, of an infection or of cells for example cancers or contaminants or bacterial resistance mechanisms. These processes can take place in a host or in an industrial process (agribusiness, paper treatment, textile).

By polynucleotide substances is understood peptides, proteins, ions, molecules or natural or synthetic chemical compositions, hormones, aromatic compounds, antibodies, antibody fragments, genes, cellular receptors, amino acids, glycopeptides, lipids, glycolipids, sugars, polysaccharides, etc . . . , capable of modifying the activity of one or more functions of an organism or of a process. These listed substances will be capable of corresponding to one or more series heads. Included is any agent capable of modifying the function or functions such as antiviral, inhibitors, stimulants, physico-chemical, radiation or thermal treatments.

The process of the invention is therefore applicable more particularly to the screening of substances capable of modifying the activity of one or more target proteins or function, implicated in a biological process thanks to the in vitro expression of said protein or proteins. The process of the invention permits the screening of multiple substances simultaneously, notably when it relates to substances liable to interact in order to express a function or to modify a function. Consequently, substance must be understood as singular as well as plural of the process of the invention described below.

Similarly, the use subsequently of the term "function" in the singular will equally cover the term "functions" in the plural and vice versa, except when it is explicitly indicated that it relates to an embodiment of the method of the invention for plural functions.

Thus, the process of the invention permits in a preferred aspect of the invention the screening of substances capable of modifying the activity of a single target protein expressed in vitro having for example an enzymatic activity, such as an amylase, a polymerase, a protease, or capable of modifying an observable property of this protein, such as for example a "DNA-binding" activity, an antigenic activity, or also capable of modifying the activity or a property of a variant of this target protein, such as for example a thermostable amylase, a more processive polymerase, a protease resistance to an anti-protease, or a "DNA binding" protein having a stronger affinity for DNA. But the process of the invention also permits the screening of substances capable of modifying the activity of a collection of proteins expressed in vitro. In this case it is the collection of proteins that make up the target of the substances to test. This collection of expressed proteins can correspond for example to the enzymes making up a synthetic pathway of a metabolite or a degradation pathway of a toxic compound, but it can also correspond to proteins making up the sub-units of a complex protein. The substances to test are therefore then evaluated for their capacity to modify the global activity of this collection of proteins, which implies that these substances can modify either the activity of all, of parts, or of a single one of the proteins of the collection, because the modification of the activity of one or of a part of the proteins leads to the modification of the activity of the collection. The process of the invention also permits the determination or screening in a second embodiment of the invention of the protein or proteins expressed in vitro capable of modifying the activity of one or more known substances.

The quality of a screening technique for substances or proteins capable of modifying the activity of a function rests principally on the effectiveness of the activity test. This test must be highly specific, sensitive, rapid and reproducible. The difficulty of these screening processes in vivo of such molecules rests among other things on the toxicity and the cellular localization (membranal barrier) of the target protein. The present invention aims to offer an isolation process with a high flow of substances or proteins capable of modifying the activity of a target protein or multiple proteins or known function permitting a leveling of the above problems.

This goal is achieved thanks to a process for the determination in vitro of the activity of a substance making use of a functional test, characterized in that a known variation of function is detected and/or measured corresponding either to one or several proteins produced in vitro or to the substance in the presence or in the absence of the proteins produced in in vitro More particularly, the process of the invention comprises the following steps:

a) the preparation of at least one nucleic acid molecule comprising the gene(s) coding for one or more proteins and the control elements necessary for transcription and translation of the gene(s), b) The transcription of the nucleic acid molecule(s) prepared at step (a), c) The in vitro translation of the transcript(s) prepared at step (b), d) The detection and/or measurement of the variation of a known function corresponding to the protein(s) produced at step (c) in the presence and in the absence of said substance, or to the substance in the presence and in the absence of the proteins produced at step (c).

The substance(s) tested in the scope of the process of the invention are introduced before, after and/or during the transcription and/or the translation of steps (b) and/or (c) and/or the detection and/or measurement of the variation of at least one known function of step (d) of the process of the invention.

In order to facilitate the discussion of the invention, at step (a) of the method of the invention under the term "gene" is designated any nucleic acid sequence permitting the expression of the protein(s) corresponding to the detected function(s). It can therefore include a DNA or RNA sequence.

The preparation of one or multiple nucleic acid molecules of step (a) of the process of the invention consists of placing the gene(s) coding for the protein(s) that will be produced at step (c) under the control of elements necessary for the transcription and the translation in vitro, that is to say under the control of a 5' promoter and possibly of a 3' RNA polymerase terminator in order to be transcribed in vitro.

A particular embodiment of the invention consists of using the promoter and the terminator of the RNA polymerase of the phage T7 or SP6 or Qβ or λ.

Similarly, in order to carry out the translation in vitro, a ribosome binding site is introduced upstream of said gene(s).

Thus as previously indicated, the process of the invention allows two embodiments according to which the function detected and/or measured at step (d) corresponds either to the protein(s) produced at step (c) or to the substance. This last case being a particular embodiment of the method of the invention.

In a first embodiment of the process of the invention, the functional test implemented at step (d) corresponds to the detection and/or to the measurement of a variation of known function of the protein(s) produced at step (b) in the presence and in the absence of a substance. The process of the invention is therefore notable in that it permits the screening of substances capable of modifying the activity of one or multiple target proteins (for example a target collection of proteins) expressed in vitro.

The gene(s) coding for the protein(s) correspond to the known function that it is desired to detect and/or measure at step (d) of the process of the invention are known or unknown, synthetic or non-synthetic genes, placed under the control of the sequences described above by classical techniques known to a person skilled in the art.

This or these genes can also be present in a sample containing nucleic acids, such as for example a soil, plant, human, animal, water, microbial culture, cellular, viral, biopsy, organism or process sample. But this sample can correspond equally to products of any method of amplification of genomic DNA, synthetic DNA, mRNA, or any nucleic acid products resulting from treatments currently used by a person skilled in the art. It is well understood that it includes a crude biological sample such as blood, tissues, urine or any other body fluid such as cerebrospinal, synovial, pleural, pericardial, or previously treated in order to prepare the nucleic acids that it contains.

One advantageous form of implementation of step (a) of the first embodiment of the present invention consists of preparing the nucleic acid molecule(s) by an amplification reaction of the gene(s) coding for said protein(s), starting from the sample of nucleic acids. It includes an amplification by PCR or by PCR-derived techniques, of the RT-PCR, nested PCR, multiplex PCR type, or techniques different than PCR of the NASPB, rolling circle or other types. Advantageously this preparation makes use of a couple of oligonucleotides or a couple of primers specific to the nucleic acid molecule(s) comprising the gene(s) coding for the protein(s) corresponding to the function analyzed. This preparation by amplification is carried out with the aid of one or multiple primer pairs, each one composed for example of PCR (FIG. 1) and NASBA:

for the sense primer, some sequence being hybridized upstream of one or multiple nucleic acid molecules comprising the gene(s) coding for said protein(s), and an RNA polymerase primer and possibly a ribosome binding site, and for the antisense primer, some sequence being hybridized downstream of one or multiple nucleic acid molecules comprising the gene(s) coding for said protein(s), and possibly an RNA polymerase terminator.

Step (a) can be carried out by any other appropriate technique. In effect, the preparation of the nucleic molecule of step (a) can be carried out by any other method known to a person skilled in the art such as a restriction cutting permitting recovery of the gene(s) of interest followed by a ligation directed with the control elements necessary for the transcription and the translation in vitro indicated previously.

As indicated previously, in a second particular form of carrying out the process of the invention, the functional test implemented at step (d) corresponds to the detection and/or to the measurement of a variation of known function of the substance. This form of carrying out, also designated functional genomics, is directed at the measurement of the variation of a known function of the substance in the presence of one or multiple proteins expressed following stages (b) to (c) of the process of the invention.

In this embodiment, step (a) consists of (i) preparing, starting from a sample containing nucleic acids, multiple nucleic acid molecules each one comprising a nucleic acid fragment coming from said sample, associated with a vector molecule, (ii) isolating each nucleic acid molecule composed of one nucleic acid fragment and one vector molecule.

The nucleic acid fragments preferably have a size from 1 to several dozens of kb, preferably from 1 to 40 kb and advantageously from 1 to 10 kb when the sample is of prokaryotic origin. These fragments can carry a partial or whole operon.

The nucleic acid fragments preferably have a size of the order of several dozens to several hundreds of kilobases in the case of a eukaryotic organism. In the particular case where cDNAs are treated at step (a), the fragments will preferably have a size of from 1 to 5 kb in the case of a eukaryotic organism.

The vector molecule is composed of one or several polynucleotide sequences comprising at least one transcription promoter for step (b) and possibly one element facilitating the isolation of the nucleic acid fragment. Advantageously this substance can be one or several streptavidine or biotin molecules, of polypyrol grouping, antibodies, a single or double-stranded polynucleotide sequence, a plasmidic DNA vector preferably not containing sequences permitting the in vivo expression of the associated fragment, or any other compound permitting the isolation of the nucleic acid fragment.

Preferably, the vector molecule is composed of two polynucleotide sequences each one comprising at least one transcription promoter, each one of these sequences being associated at one end with one of the nucleic acid fragments. The transcription promoter(s) carried by the vector molecule are preferably of the strong type.

The vector molecule associated with each fragment of step (b) is advantageously a plasmidic vector preferably not permitting the expression of said fragment in vivo.

In the second embodiment of the invention, the biological sample from which the nucleic acid molecules of step (a) are prepared can come from one or several prokaryotic organisms or eukaryotic cells, or also from identical or different viruses, but it can likewise be composed of a sequence or of a bank of synthetic nucleic acids or also composed of organisms and/or unknown nucleic acids. It can also comprise a eukaryotic DNA bank and then the transcription reaction of step (b) is completed by a splicing reaction and by in vitro maturation of the mRNA by using a nuclear extract.

As indicated above, according to a particular embodiment of the process of the invention, the vector molecule associated with the nucleic acid fragments is a plasmidic vector. In this case, each fragment is inserted in a vector at the level of a cloning site or of a restriction cassette. This plasmidic vector is characterized in that it comprises an RNA polymerase promoter at one side of the cloning site and possibly an RNA polymerase terminator at the other side. It is also possible to envision a vector comprising a cloning site surrounded by two identical or different RNA polymerase promoters and possibly flanked on both sides by a corresponding RNA polymerase terminator or terminators. These promoters and possibly terminators preferably have the characteristic of not functioning in the microorganism that can be used for the separation of recombinant vectors at the step.

In the case where the vector does not possess a promoter or promoters and/or possible RNA polymerase terminator(s), or in the case where the promoter(s) and possible RNA polymerase terminator(s) are not adequate for carrying out step (b), this promoter or promoters and possible terminator(s) can be inserted by any appropriate means. An advantageous implementation of this insertion consists of carrying out a PCR with a set of primers carrying the sequences of the promoter(s) and terminator(s). According to a particular way of implementing the process of the invention, the promoter(s) and possible terminator(s) are of the strong type such as for example those of the T7 or SP6 or Qβ RNA polymerase.

In the case where the vector molecule is a plasmidic vector, the isolation of the recombinant can be carried out by transformation of host cells by the collection of recombinant vectors in a way so as to create a bank of clones, then there is carried out an extraction of the vector or of a part of the recombinant vector contained by each clone of the bank by any appropriate means.

The extraction of the recombinant vector or of a part of the recombinant vector flanked by promoter(s) and possible RNA polymerase terminator(s) can be carried out by any method known to a person skilled in the art, such as by mini preparation and possibly digestion or by PCR. An advantageous alternative consists of carrying out this PCR with oligonucleotides protected at the 5' end from nucleasic attacks, notably from the nucleases contained in the translation medium, by phosphorothioate groups.

As indicated previously, the isolation of the nucleic acid molecules can be carried out by any physical, mechanical or chemical means such as for example a simple extreme dilution of the collection of the fragments associated with the vector molecule. But the isolation can also advantageously be carried out by using the properties of a specific substance included in the vector molecule, such as an antibody molecule, and the isolation of the fragment is carried out by using the antibody-antigen affinity; or a biotin, and the isolation is carried out by using the biotin-streptavidine affinity, etc . . . .

The screening process according to the invention lends itself to several ways of being implemented notably according to the type of activity of the target protein(s). In effect, the target gene(s) prepared at step (a) can encode for one or several target proteins or functions implicated in diverse types of biological processes. This gene or genes can come from several prokaryotic organisms or from eukaryotic cells or also from viruses. As indicated previously, a process can be for example an infectious disease, a bacterial or viral resistance mechanism, a metabolic chain or also a process implicated in an agribusiness industrial process, of paper treatment, of detergent preparation, of textile manufacturing etc . . . .

Transcription step (b) and the translation phase of step (c) can be simultaneous, which means that the translation phase of step (c) is carried out simultaneously with the transcription of step (b) or decomposed in two distinct steps (b) of transcription and (c) of translation.

The breaking apart of steps (b) and (c) permits optimization of the yields of each step, and thus production of more significant quantities of proteins, which finds its main utility in the case of detection of enzymes of weak specific activity.

This breaking down also permits normalization of the formation of the products at step (c) and of being able to later compare the different functions expressed.

The breaking down between the transcription of step (b) and the translation of step (c) equally permits avoidance of the problems of degradation of the DNA matrix by the nucleases if they were prepared by PCR. In effect, the constituents of the transcription reaction are less contaminated by nucleases, contrary to the translation extracts.

The breaking down moreover permits the use of different translation extracts according to the origin of the targeted DNA. In effect, the translation phase of the transcript at step (c) is advantageously carried out with a translation extract of the same origin or of an origin close to that of the biological sample of which the process of the invention is practiced. Thus, the adequacy between the origin of the translation signals of the transcripts and the translation extract is optimized for optimal translation efficiency. There can be cited by way of example the use of a translation extract of an extremophilic organism if the preparation at step (a) makes use of a nucleic acid sample coming from the same organism or from another extremophilic organism (thermophiles, halophiles, acidophiles, etc . . . ) or also a translation extract of eukaryotic cells if the preparation at step (c) makes use of a eukaryotic nucleic acid sample. These respective extracts are capable of improving the effectiveness of the process. These extracts are chosen for their capacity to translate the transcripts of step (c).

The process of the invention is notable in that it makes use of an adequacy between the expression punctuation of the transcripts of step (b) and the translation extracts used. These extracts are also characterized in that either they do not contain the sought-after function, or they contain it but it is not detectable under the conditions of the test carried out in order to detect the sought-after function. It includes for the example the use of a translation extract containing a mesophilic beta-galactosidase activity permitting translation of a thermophilic beta-galactosidase mRNA and the detection of the activity of the latter at high temperature, which eliminates the mesophilic beta-galactosidase activity.

According to the genetic origin of the genes obtained at step (a), for example DNA of Gram positive, or negative microorganisms, of eukaryotes of viruses, etc . . . , and to the function tested, different translation extracts can therefore be used.

A particular implementation of the process of the invention consists of using at step (c) a translation extract that in fact is a mixture of several translation extracts. It includes for example a translation extract of E. coli overexpressing a chaperon A protein mixed with a translation extract of E. coli overexpressing a chaperon B protein. Any type of mixture can be contemplated once it corresponds to the characteristic described above. In the same manner, it is possible to use a translation extract in which one or several specific tRNAs of one or of several codons is added. The translation extracts thus obtained then permit translation of the mRNA containing these specific codons, such as for example the translation of an mRNA containing an amber codon by adding in the translation extract a tRNA suppressor or suppressors.

The treatment of step (c) with a translation extract can also be carried out with a universal translation extract whatever be the origin of the sample such as for example an E. coli extract and/or any other cellular extract(s) supplemented or not by molecules of interest such as those, for example, previously indicated (tRNA, chaperon . . . ).

It is equally possible to add to the translation extract of step (c) one or several substances favoring a more efficient refolding or maturation of the expressed proteins, such as for example chaperons, detergents, sulfobetaines, membranal extracts, etc . . . .

The detection and/or the measurement of the variation of at least one known function corresponding to the protein(s) produced at step (c) or to the substance is carried out by any functional test known to a person skilled in the art such as defined in the introduction. Step (d) can thus consist of detecting and/or measuring several variations of functions corresponding to one or several of the proteins produced at step (d) or corresponding to one or several substances.

The variations of function(s) are detected our measured in a direct or indirect manner by one or several functional test(s) of the protein(s) produced at step (c) or of the substance(s) to screen. The function(s) is/are read for example continuously for example by fluorimetry or by colorimetry or by viscosimetry or by mass spectrometry . . . .

The detection and/or measurement of the variation of function corresponding to the protein(s) produced at step (c) or to the substance(s) is advantageously carried out at step (d) by a functional test making use of the presence at one of steps (a), (b), (c) or (d) of one or several reporter molecule(s) permitting detection and/or measurement of the activity of the protein(s) produced at step (c) or of the substance(s) to screen corresponding to the function analyzed at step (d).

The process of the invention presents the following advantages as much in its first as in its second embodiment:

The fact of directly working on the activity of the protein (s) produced at step (c) or on the activity of the substance permits good specificity of the screening test.

The sensitivity of the test is explained by the multiplier coefficient of the enzymatic steps (b) and (c), corresponding respectively to transcription and translation, and possibly to the functional test making use of an enzyme.

The process of the invention is fast because entirely automated. For example, a plaque of 384 wells can be treated in 2 to 3 hours.

Finally, the reproducibility is facilitated by the absence of storage of the protein(s) produced at step (c). Additionally, the protein(s) is/are expressed in vitro independently of a complex and not always controllable cellular context (membranal diffusion, cellular localization, cellular toxicity, cellular physiology, induction or repression problems, etc . . . ).

The process of the invention is therefore notable because besides the carrying out of a screening of one or several functions, of a substance it also permits:

development of new functional tests doing functional genomics.

The process of the invention in effect permits development of new functional tests. We have witnessed these last years a rapid expansion of high flow screening test or "high throughput screening (HTS)". These screenings, in order to be optimal, require the implementation of sensitive functional tests, but one does not always have these functional tests at one's disposal. The process of the invention permits the identification of one or several functional test(s) permitting the improvement of the revelation of one or several function(s) of a process or of an organism, and thus the improvement of the measurement of the variation of this function or these functions in the presence or in the absence of one or several substance(s).

Thus, it is possible to develop new functional tests notably of the following fashion:

a) The preparation of at least one nucleic acid molecule comprising the gene(s) coding for one or several proteins and the control elements necessary for transcription and translation of the said gene(s).

b) The transcription of the nucleic acid molecule(s) prepared at step (a).

c) The translation in vitro of the transcript(s) prepared at step (b).

d) The detection and/or the measurement of the variation of a known function corresponding to the proteins produced at step (c) in the presence and in the absence of one or several reporter molecule(s).

e) Thus in the scope of this application the substance corresponds to the reporter molecule capable of revealing a function.

The process of the invention in its first and second embodiment presents a real advantage for the functional genomics.

The process of the invention is more particularly applicable to after-sequencing genomics. The project of decoding the human genome has given birth to a new genomic science, now present in the heart of therapeutic enterprise. Genomics permits identification and description of the genes which direct the manufacture and the putting together of all of an organism's molecules. These genes coding for the functions of organisms or of processes can be expressed by the process of the invention, which permits confirmation of the function encoded by a reading frame located by bioinformatics, of highlighting one or several pharmaceutical substances capable of modifying said function encoded by one or several proteins expressed by the process of the invention or which will permit identification of the targets of a substance corresponding to one or several functions of an organism or of a process expressed at step (c).

In 100 years of existence, the pharmaceutical industry has identified several hundreds of receptor sites. With functional genomics, other existing receptor sites can be attained, as many potential target functions for future substances that remain to be contemplated.

By way of example of such an application, the spotting by bioinformatics of an ORF possibly encoding a target, confirmation of this target by the process of the invention and finding for it substances which can make its activity vary can be cited.

Another example of functional genomics consists of identifying at the genetic level a gene corresponding to a protein whose activity is modified by one or several substances. In the case where the effect of a pharmaceutical substance on an organism or a process is known, this application of the process of the invention presents a particular interest. The genes corresponding to the proteins encoded by this organism or this process will then be prepared according to a particular implementation of step (a) described previously, in a manner so as to isolate said genes and express them at steps (b) and (c) of the process of the invention. A functional test at step (d) permits measurement of the activity of the substance in the presence and in the absence of each one of the proteins expressed at step (c). The measurement at step (d) of a variation of activity of the substance in the presence and in the absence of proteins expressed at step (c) then permits identification of the protein(s) whose activity is modified by said substance within the organism or the process.

This embodiment of the invention presents the enormous advantage of being able to go directly up to the gene starting from the protein(s) expressed at step (c) and isolated at step (a). The functional target can thus be identified at the genetic level of one or several substances.

Each time that a functional test can be implemented (enzymatic test, binding test, etc . . . ), the process of the invention permits high flow subjecting of the collection of the expressible proteins of a considered organism to an automated functional test and of going up in a few hours to the gene corresponding to the sought-after function.

The description which follows preferably refers to examples of carrying out the first embodiment of the process of the invention in which the protein(s) corresponding to the function(s) detected and/or measured at step (d) are designated target protein(s) and the corresponding coding gene(s) is/are designated target gene(s). Thus, the process of the invention permitting screening of the substances capable of modifying the activity of a target protein or of several target proteins expressed in vitro includes the following steps:

a) the preparation of at least one nucleic acid molecule comprising the gene(s) coding for the target protein(s) and the control elements necessary for the transcription and the translation of said target gene(s).

b) the transcription in vitro of the nucleic acid molecule(s) prepared at step (a).

c) the translation in vitro of the transcripts of step (b).

d) the detection and/or the measurement of the variation of at least one known function corresponding to the target protein(s) produced at step (c) in the presence and in the absence of the substance to screen.

As previously indicated, the process of the invention permits detection and/or measurement at step (d) of the variation of one or several functions corresponding to one or several target proteins produced at step (c). It refers for example to proteins expressed by an operon. Consequently, the process of the inventions lends itself to several forms of being carried out.

When it relates to the screening of substances capable of modifying a function corresponding to the activity of a target protein, the process of the invention includes the following steps:

a) the preparation of a nucleic acid molecule comprising the gene coding for said protein, 5' of said gene an RNA polymerase promoter and a ribosome binding site and possibly an RNA polymerase terminator 3' of said gene.

b) the transcription in vitro of the nucleic acid molecule prepared at step (a), c) the translation in vitro of the transcripts of step (b), d) the detection and/or the measurement of the variation of at least one known function corresponding to the target protein(s) produced at step (c) in the presence and in the absence of the substance to screen.

But the process of the invention can also be applied to the screening of substances capable of modifying the function corresponding to a collection of target proteins. The genes coding for these proteins can be located on the same DNA fragment as in the case of an operon, or at different places of the genomic DNA as in the case of certain metabolic pathways.

When the process of the invention relates to the screening of a substance capable of modifying the activity of a collection of proteins, step (a) of the process lends itself to the following two embodiments:

i) Either, the genes are grouped together under the form of an operon, and then step (a) consists of preparing a nucleic acid molecule comprising the genes (the operon) coding for the proteins, 5' of the collection of said genes (of the operon) an RNA polymerase promoter, possibly 3' of the collection of said genes (of the operon) an RNA polymerase terminator, and for each of said genes its natural ribosome binding site.

ii) Or, said genes are separated and then step (a) consists of preparing one or several nucleic acid molecules comprising the genes coding for the proteins, 5' of each one of said genes an RNA polymerase promoter and a ribosome binding site, and possibly 3' of each one of said genes an RNA polymerase terminator.

In the first embodiment (i) above, the ribosome binding site of each one of the genes is its natural ribosome binding site, and it is then preferred to use at step (c) a translation extract prepared starting from the organism from which the target gene(s) come from or from a phylogenetically close organism.

In the second embodiment (ii) above, the ribosome binding site can be the natural site of each one of the genes or another ribosome binding site more adapted to the translation step (c).

A variant of the first (i) and of the second (ii) embodiment of the above process consists of carrying out in parallel or simultaneously the previously described process of the invention with a single protein, each step (a) being carried out with each one of the genes. An alternative to the parallel or simultaneous carrying out of the process of the invention, consists of separately carrying out for each one of the genes the steps (a), (b) and (c), then, for the final screening implicating each one of the proteins, gathering the products of the steps (c) together in order to carry out step (d).

Similarly, when the process relates to screening substances capable of modifying the activity of a collection of proteins in which the genes are physically separated on the organism's genome, the process of the invention consists of carrying out in parallel or simultaneously, the process of the invention previously described with a single protein, each step (a) being carried out with each one of the genes. An alternative to the carrying out in parallel or simultaneously of the process of the invention, consists of separately carrying out for each one of the genes, the steps (a), (b) and (c) then, for the final screening implicating each one of the proteins, to collect the products of the steps (c) in order to carry out step (d).

As previously indicated, the process of the invention permits screening of the substances capable of modifying the activity of a collection of target proteins. The process of the invention can therefore be applied to the screening of substances capable of modifying the activity of the variants of a protein or of the variants of a collection of proteins. The gene(s) corresponding to this variant or these variants can be contained for example in the same nucleic acid sample from the start. By way of example of this application of the process of the invention, the different mutants of the VIH protease gene contained in a sample of a patient infected by this virus can be cited. The implementation of the process of the invention then consists of carrying out each step (a) with each one of the mutants of said gene in such a way as to express each one of them separately. The separation of the mutants contained in the sample can be carried out by cloning, extreme dilution, or by any other method known to a person skilled in the art. This application of the process of the invention therefore consists of screening all of the substances to test not on a target protein or on a collection of target proteins but on all the existing variants of them, of which the corresponding genes are contained in a single sample of nucleic acids. This application of the process of the invention therefore permits the determination of the spectrum of action of the substances to test.

The invention therefore also relates to the application of the screening process to substances capable of modifying the different variants of a target protein or of a collection of target proteins. In effect, as indicated above for the VIH protease, the sample of a patient infected by this virus can contain several variants of the virus each one expressing a different protease. It is therefore interesting to carry out a screening on each one of the different proteases in order to determine those that are inhibited by the known antiproteases or those that can be by new substances to test.

On the basis of this example of the HIV virus, the invention permits the analysis in vitro of the different variants of a target protein or of a collection of target proteins. This goal is attained according to the invention, by possibly amplifying the different mutants, for example by cell culture or by molecular amplification, then by isolating each mutant gene, for example by cloning or by extreme dilution, and by expressing each one of these genes in accordance with steps (a), (b) and (c) of the process of the invention, and finally by screening the substances capable of modifying the activity of the protein(s) produced during step (d). The screening process consists for example in the case of the VIH proteases of carrying out an inhibition test with the different inhibitors or the different substances to test on each protease individually. The activity of each one of the proteases expressed in accordance with the process of the invention can then be characterized in such a fashion as to reveal the representation of the different variants of the virus that infect a patient. The result of the screening process according to the invention then permits adapting the therapy of the patient.

As stated previously, the functional test can be used for one or several reporter molecules. In a first particular embodiment of the process of the invention, the reporter molecule must be present at step (c) or (d) to reveal the possible activity of the target protein according to the role of the substance tested during the screening.

But the reporter molecule can also be present in the reaction mixture from one of the steps (a) to (b), either under its final reporter molecule form, or, according to a particular embodiment of the invention, under the form of a nucleic acid molecule (DNA or RNA) corresponding to the gene coding for said reporter molecule, and then designated hereinafter reporter gene. In this particular embodiment, the reporter molecule will advantageously be produced during step (c) conjointly with the target protein(s).

Thus, according to a particular embodiment of the screening process of the invention, the reporter molecule is a protein that is produced during step (c) conjointly with the target protein(s). Advantageously, in this embodiment of the process of the invention, the gene coding for the reporter molecule is placed under the control the transcription and translation regulation sequences similar to that of the gene(s) coding for the target protein(s), in a fashion such that the reporter gene is co-expressed with the target gene(s).

By way of example, the reporter gene can be the gene of the GFP protein (Green Fluorescent Protein) or that of the beta-lactamase (TEM-1). In the case of the GFP, it is the fluorescence emission that is evaluated. It is then possible to carry out a test such that the GFP only fluoresces if the activity of the products of the target gene(s) is modified by the molecule(s) tested. In the case of the beta-lactamase, it is the activity of this enzyme that is evaluated by incubating a fraction of the translation reaction in a buffer containing nitrocephine. Nitrocephine is a chromogenic beta-lactamine that has the property of changing color from yellow to red when it is hydrolyzed by an active beta-lactamase. A yellow tests indicates for example that the molecule(s) tested is(are) capable of modifying the activity of the target gene product.

Any other reporter gene can be contemplated in the process of the invention, such as those of beta-galactosidase, luciferase, peroxidase, or a microperoxidase, etc . . . . It is worth noting that the GFP reporter gene has the advantage of producing a protein whose activity is instantly measurable, which permits a supplemental savings in time. But, a reporter gene coding for a protein having a beta-lactamase type enzymatic activity has a large sensitivity due to the enzymatic multiplier coefficient.

A particular embodiment of the process of the invention with a reporter gene consists of expressing in vitro a reporter gene within which one or several genes coding for the protein(s) have been inserted, the collection of these genes being under the control of the same transcription and translation regulatory sequences.

An example of a nucleic acid molecule prepared at step (a) corresponding to this embodiment of the process of the invention is represented at FIG. 2 attached. This particular case, where the target gene and the reporter gene are co-expressed, is quite adapted to the target gene corresponding to the inteins such as the *Mycobacterium tuberculosis* RecA intein.

Another particular embodiment of the process of the invention with a reporter gene consists of using a target gene (coding for a target protein or a function) that can itself be a reporter gene. An example of a nucleic acid molecule prepared at step (a) corresponding to this embodiment of the process of the invention is represented at FIG. 3 attached. This embodiment is particularly adapted to a target protein having a directly detectable activity in vitro, such as an enzymatic activity, such as beta-lactamase. The beta-lactamase gene plays an essential role in the resistance to beta-lactamine type antibiotics by hydrolyzing these molecules before they have been able to act on their therapeutic targets. Thus, once the enzyme has been put in the presence of the molecules to test at step (b), (c) or (d), the beta-lactamase activity can be evaluated thanks to a nitrocephine test.

The steps of the process of the invention can be carried out successively without interruption by the same operator, advantageously on an automated device integrating each one of the steps, or can be carried out discontinuously, possibly by different operators.

If the tested substance corresponds to a polynucleotide sequence, it will be able to have a role as such or as a gene coding for a protein. In this latter case, this polynucleotide sequence possesses all the sequences necessary for its in vitro expression during the transcription and translation reaction. Preferably, it will be expressed by the same regulatory sequences as the target gene(s) in order that their expression will be concomitant and that the molecule will have the time to modify the activity of the products of the gene(s) expressed after steps (b) and (c). This avoids generation of false positive or false negative results.

One of the possible roles of the substances to screen is to slow down, even to stop, in vitro, the activity of a target protein or of a collection of target proteins, which can be implicated for example in the progression of a disease. These molecules will for example be resulting from libraries having a particular pharmacological interest, resulting from work in combinatorial chemistry taking into account the structure of pre-existing productive inhibitors and/or the structure of the target enzyme active site and its particular characteristics.

But the tested substances in the scope of the process of the invention can equally have a stimulator or activator effect on the activity of the product of one or several target genes having a key role in processes. Such molecules can prove useful insofar as enzymatic cofactors permitting reduction of the enzyme activity in a given industrial phenomenon (agribusiness or other) and thus to increase in yield.

Each time that a tested substance is proven effective for modifying the activity of the target protein, it is advantageous to verify, by an appropriate method, that this substance does not inhibit one of the steps of the process. Moreover, after having identified a substance capable of modifying the activity of a target protein, this protein can be tested according to the process of the invention on proteins having an activity similar to that of the target protein(s).

The process of the invention can advantageously be implemented on any type of support and is therefore easily capable of being automated. By support is understood for example microtitration plaque wells and equally biochips. They can contain several dozens to several thousands of sites. Thus, on a single support from dozens to thousands of substances will be able to be tested for their capacity to modify the activity coded by the target gene(s) of one or several nucleic acid molecules prepared at step (a).

A particular embodiment of the process of the invention consists of charging the wells of these plaques with a coupled transcription and translation reaction mixture (components necessary for transcription and translation) containing one or several nucleic acid molecules prepared at step (a) and the reporter molecule, then to freeze them to avoid the premature initiation of the transcription/translation reaction. The frozen plaques are placed on an automatic machine, which deposits in each well a volume of the molecule to test permitting dilution of the transcription and translation mixture until it is concentrated 1 time. A homogenization can be contemplated through the automatic machine, but the reaction volumes should be sufficiently small in order for the diffusion to assure this homogenization.

The measurement of the activity of one or several target proteins or of the reporter molecule of step (d), and therefore of the effect of the tested substance on the target protein or on a collection of target proteins, can be equally advantageously automated. The possible modification of the target protein activity is directly read on the support in a fluorimetry reader (if the reporter is for example GFP) or in a fluorimetry reader (if the reporter is for example beta-lactamase). The automated readings will be adapted for the revelation of the reporter. It is thus possible to carry out a reading of the reporter activity continuously.

The automation presents advantages in terms of the potential screening. The process of the invention can be contemplated in a micro-manufacturing concept in such a manner as to manipulate on a unique support thousands of reaction nanovolumes. This represents a certain advantage in terms of cost but equally in high flow screening potential. The process of the invention implemented on a biochip permits screening of collections of substances for example resulting from combinatorial chemistry work having for example antifungal or antibacterial or antiviral or anticancer properties or from collections of substances directed against diseases such as Parkinson's or Alzheimer's. The process of the invention applied at high flow permits identification of the substance key best adapted to a function lock given in a minimum time. It therefore permits the rapid and systematic testing of all of the possible combination of a set of given substances.

Consequently, the invention relates to a device comprising an arrangement of one or several supports, of robots and of a reader of said supports for the carrying out of the stages of the process of the invention.

Finally, the invention has for an object a kit for screening substances capable of modifying the activity of one or several functions in vitro in accordance with one of the embodiments of the process of the invention.

In a first embodiment, such a kit includes the means for revealing the function, an RNA polymerase, nucleotide sequences for the preparation of nucleic acid molecules comprising the gene(s) permitting the expression of the protein(s) corresponding to the detected and/or quantified function, the four triphosphate nucleotides, the mixtures necessary for said preparation, for the transcription and the translation, possibly some substances, possibly some controls.

In a second embodiment, a kit according to the invention comprises:
- possibly substances necessary for the preparation of the nucleic acid molecules comprising the gene(s) permitting the expression of the protein(s) corresponding to the quantified and/or detected function,
- any support such as a microtitration plaque or chip containing: the means for revealing the function, an RNA polymerase, the four triphosphate nucleotides, the transcription and translation mixtures, possibly some controls.

The kits and the supports can be contemplated for the detection and/or the measurement simultaneously or not of a variation of one or several function of one or several processes or of one or several organisms.

The invention therefore also has as an object a support having a series of sites for the implementation of a method of the invention, characterized in that each one of said sites permits the detection and/or the measurement of a variation of function.

The substance to screen can be present in the wells or can be added at the end of the reaction.

Other advantages and characteristics of the invention will appear in the examples of carrying out the invention which follow and which make reference to the attached drawings in which:

FIG. 3 is a schematic representation demonstrating the process of the invention with Beta-lactamase suicide inhibitors.

FIGS. 4, 5 and 6 represent the comparison of the sensitivity and of the reproducibility of the several methods of detection of a function according to the process of the invention.

FIG. 7 represents the effects of different substances (0.4 $\mu$M final) on the variation of the TEM-1 beta-lactamase activity.

FIG. 8 represents the effects of different substances (21.5 $\mu$M final) on the variation of the TEM-1 beta-lactamase activity.

FIG. 9 represents the characterization of the inhibitor resistance.

FIG. 10 represents the effect of different substances (2.5 $\mu$M final) on the variation of the activity of the HIV virus protease at t=0 min. and t=180 min.

EXAMPLE I

Figure 1:
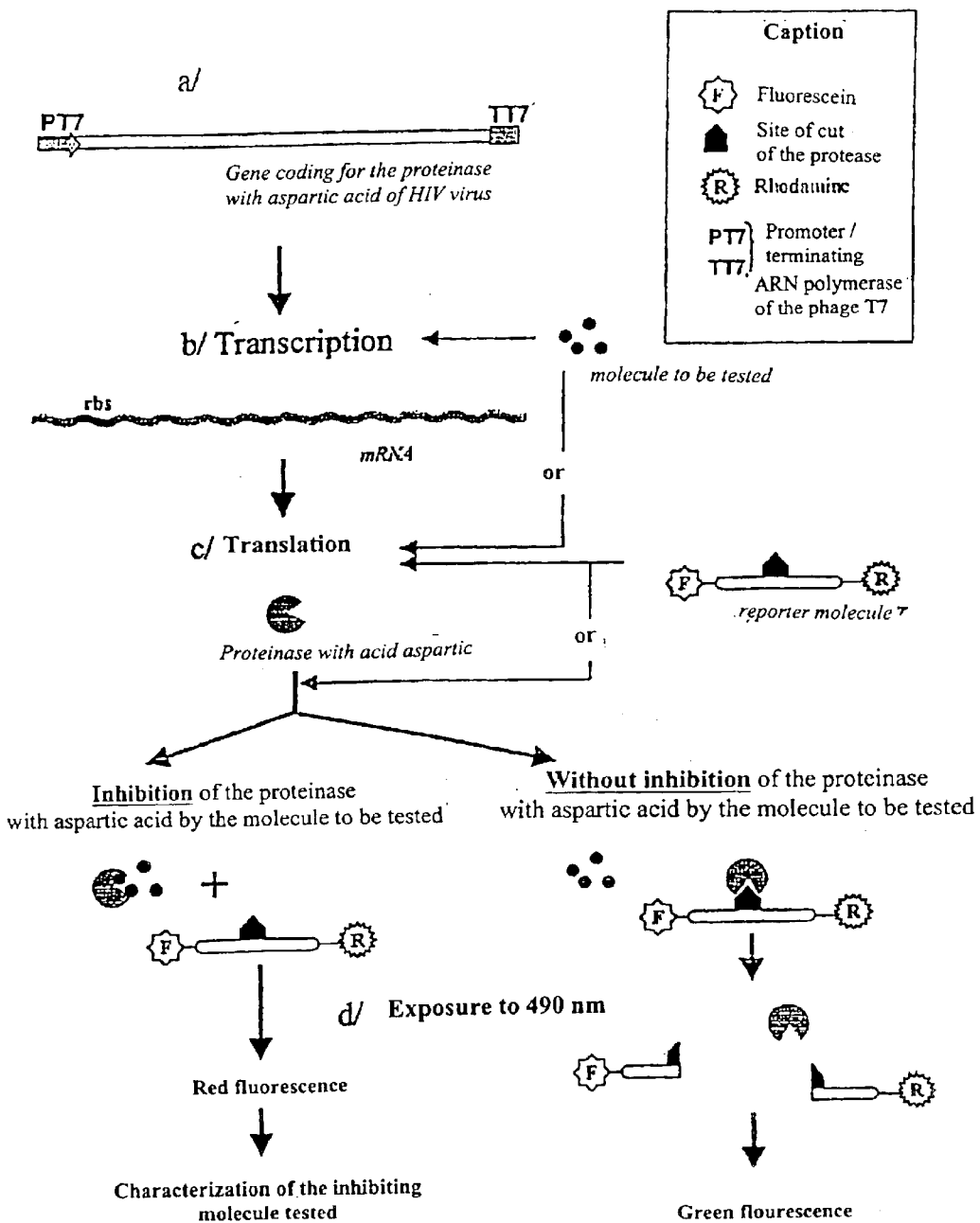
FIG. 1 is a representation demonstrating the process of the invention with an aspartic acid proteinase inhibitor of the HIV virus.

Effects of the Substances A, B, C, and D on a Sample Function

The tables below illustrate different results capable of being obtained by the process of the invention on a sample comprising a function. The measurement of signal variation is carried out by any technique known by a person skilled in the art. The signals are measured according to their property, in a direct manner or not, which may or may not require the presence of a reporter. It is contemplated that the signal(s) will be read continuously under a kinetic form for example. The method of the invention therefore offers a large choice of ways of being carried out starting from the functions and means implemented for revealing it/them.

By variation in signal is understood in the presence of a substance (table 1):

An increase of the activity that may or may not depend on the quantity of substance(s) added.

A decrease of the activity that may or may not depend on the quantity of substance(s) added.

An inhibition of the studied activity that may or may not depend on the quantity of substance(s) added.

1) Table 1 below shows that the substance A permits an increase in the functional activity. The larger the quantity of A present, the more the function is active.

TABLE 1

|  | Signal |
| --- | --- |
| Without substance | 0 |
| In the presence of a substance A | ++ |
| In the presence of twice as much of a substance A | ++++ |

2) Table 2 above shows that substance B has the same effect on the faction whatever its quantity.

TABLE 2

|  | Signal |
| --- | --- |
| Without substance | 0 |
| In the presence of substance B | + |
| In the presence of twice as much substance B | + |

3) Table 3 below shows that the substance C has no effect on the function. On the other hand, beyond a threshold 2C, substance C has a negative effect on the function.

TABLE 3

|  | Signal |
| --- | --- |
| Without substance | + |
| In the presence of substance D | 0 |
| In the presence of twice as much substance D | 0 |

EXAMPLE II

Measurement of the Variations of Activity of the Functions 1 and 2 in the Presence of a Substance The process of the invention also permits studying the effect of a substance on one or several functions. In effect, a substance is liable to act on the active site of two different functions. This is the case for example for bivalent chelator ions such as EDTA that inhibits the metalloproteinases and polymerases at the same time (these two enzymes needing bivalent ions in order to function). On the other hand, it is equally possible that the effect of a substance on a function induces secondary metabolites responsible for variation of the activity of one or several other functions. The tables below illustrate these different results.

1) Table 5 below shows that the substance A permits increasing the activity of a function 1 and inhibits a function 2.

TABLE 5

|  | Function 1 | Function 2 |
| --- | --- | --- |
| Without substance | + | + |
| In presence of substance A | +++ | 0 |
| In presence of twice as much substance A | ++++ | 0 |

2) Table 6 below shows that the substance A permits increasing the activity of a function 1 but little for that of activity 2. On the other hand once function 1 activated, there is an activation of function 2. But in the presence of too large a quantity of A, there is an over-activation of 1 that induces an inhibition of 2.

TABLE 6

| Function 1 | Function 1 | Function 2 | Functions 1 and 2 |
| --- | --- | --- | --- |
| Without substance | + | 0 | + |
| In the presence of substance A | +++ | ++ | +++++ |

TABLE 6-continued

| Function 1 | Function 1 | Function 2 | Functions 1 and 2 |
| --- | --- | --- | --- |
| In the presence of twice as much substance A | +++++ | 0 | +++++ |

EXAMPLE III

Effects of a Combination of Substances on a Function of a Sample

Another embodiment of the process of the invention consists of testing several substances on a function. These substances can be added in a combined or sequential manner to each one of the steps of the process. The test of several substances on a function is going to permit determination if these substances have a cooperative or an antagonistic effect among themselves, if they are competitive or complementary among themselves. The process of the invention permits testing all possible combinations of substances one or several functions.

1) Table 7 below shows that the substance A increases the functional activity. The substance B is without effect on the function. The substance A and substance B couple still increases the activity of the function more than substance A alone. Substance B an effect complementary or cooperative of substance A.

TABLE 7

|  | Signal |
| --- | --- |
| Without substance | 0 |
| In the presence of substance A | ++ |
| In the presence of substance B | 0 |
| In the presence of substances A and B | ++++ |

2) Table 8 below shows that the functional activity is increased in the same fashion in the presence of substance A alone or substances A and B. Substance B therefore does not have any effect on the function, as it is shown in the functional test in the presence of substance B alone.

TABLE 8

|  | Signal |
| --- | --- |
| Without substance | 0 |
| In the presence of substance A | ++++ |
| In the presence of substance B | 0 |
| In the presence of substance A and B | ++++ |

3) Table 9 below shows that the substances A and B separately and the A and B substances couple inhibit the function.

TABLE 9

|  | Signal |
| --- | --- |
| Without substance | + |
| In the presence of substance A | 0 |
| In the presence of substance B | 0 |
| In the presence of substances A and B | 0 |

4) Table 10 below shows that the substances A and B separately do not have any action on the function, whereas the couple of substances A and B increases the activity of the function.

TABLE 10

|  | Signal |
| --- | --- |
| Without substance | 0 |
| In the presence of substance A | 0 |
| In the presence of substance B | 0 |
| In the presence of substance A and B | +++ |

EXAMPLE IV

Effects of a Combination of Substances on One or Several Functions

The variations of one or several functions obtained in the presence of one or several substances can be compared between them to determine the best substance(s) or the best combination of substances as well as the best quantity of each substance.

The process of the invention can therefore equally be implemented for studying the different galenic forms of one or several substances. After having identified one or several substances capable of modifying the activity of one or several functions, these substances will be used to treat a product. The galenic form of the substance(s) will be important for an optimal efficiency of said substance(s) on the function(s) of the product(s). This is why the component(s) of the galenic form can be added to said substance(s) in the process of the invention to study their impact on the variation of activity of one or several functions.

EXAMPLE V

Follow-up of the Effectiveness of One or Several Substance(s) on One or Several Function(s) of One or Several Organism(s) or Processes The process of the invention equally permits following the behavior of one or several functions in the presence of one or several substances.

In other words, it permits studying the effectiveness of one or several substance(s) (table 11). In subjecting one or several organism or process functions to one or several substances, it is possible to induce variations of said function(s), which makes them no longer have the same behavior vis-à-vis one or several substances. By treating one or several function by one or several substances, it is subjected somewhat to a selection pressure. This or these functions can for example become tolerant vis-à-vis one or several substances or they can have resistance phenomena. Thus, the effect of a treatment of one or several functions of an organism or process to one or several substances, can be tested by the process of the invention by measuring for one or several function their variation of activity in the presence of said substance(s). This particular embodiment of the process of the invention will also permit an evaluation of the toxicity of one or several substances on one or several functions of an organism or process.

It thus also relates for example to a follow-up of the evolution of one (or several) functions when they are subjected to the presence of one (or several) substances.

Table 11 below illustrates this type of result on the toxicity of a substance A on the functions 1 and 2. Table 11 shows at time t, that a substance A increased the activity of a function 1 that continues to increase until time t+1. On the other hand, at time t+2, the substance A has lost its effectiveness on the function 1. The function 1 therefore becomes less sensitive to the effect of the substance A with time. Table 11 also shows that the substance A inhibits the function 2 more and more with time.

TABLE 11

|  | Function 1 | Function 2 |
| --- | --- | --- |
| In absence of substance | + | +++ |
| Measurement at time t in the presence of substance A | ++ | ++ |
| Measurement at time t + 1 in the presence of substance A | ++++ | + |
| Measurement at time t + 2 in the presence of substance A | + | 0 |

The process of the invention therefore permits an assessment of the effectiveness of the best substance(s) capable of best making the activity or activities of said functions vary with time.

EXAMPLE VI

Screening at High Flow Rate of Aspartic Acid Proteinase Inhibitors

Among the viral proteins necessary to the multiplication cycle of the HIV virus, aspartic acid proteinase can be noted, used as a target in different antiviral therapies (such as for example tritherapy). Research of powerful aspartic acid proteinase inhibitors is in full expansion taking into account the adaptation of the virus to the inhibitors: 6 weeks after the beginning of a therapy with an HIV-1 proteinase inhibitor (indinavir), isolates resistant to the inhibitor are detected. They manifest themselves, among other things, by a mutation at the level of the HIV-1 proteinase V82A/F/T residue (4). The objective of different pharmaceutical laboratories is therefore to develop a high flow rate screening system in order to find numerous aspartic acid proteinase inhibitors.

The following screening test of new aspartic acid proteinase inhibitors (HIV) rests on the process of the invention. The target gene coding for the native HIV aspartic acid proteinase is placed under the control of the T7 phage RNA polymerase promoter and terminator, which permits the transcription and the translation of the corresponding protein in vitro.

The reporter molecule used at step (d) is a peptide containing specific cutting sites of the HIV proteinase. This peptide is covalently linked respectively at the N and C terminus to a fluorescent molecule (such as for example fluoresceine) and to a quencher of the latter (such as for example rhodamine).

The gene prepared at step (a) is placed in different wells of a microtitration plaque. The corresponding wells are charged with a concentrated coupled transcription and translation reaction mixture (concentrated components necessary for the transcription and for the translation) containing the reporter molecule. The corresponding plaques are rapidly frozen to avoid the premature initiation of the transcription and translation reaction. This transcription and translation reaction can be carried out either with a cellular E. coli translation extract or with a eukaryotic cell translation extract. The translation extract chosen depends on the type of primers used in (a) with or without a ribosome binding site. The frozen plaques are placed on an automatic device, which deposits in each well a volume of the substance(s) to test permitting dilution of the transcription and translation mixture until it has been concentrated one time.

If this substance is as active as the target protein inhibitor, it prevents the HIV aspartic acid proteinase from attacking the reporter molecule. Fluoresceine and rhodium are then found in a sufficiently close environment to assure an FRET (fluorescence resonance energy transfer) energy transfer After exposure of the reporter peptide to a given wavelength (about 490 nm), only the red fluorescence of the quencher will be detectable.

If the tested substance is not capable of inhibiting the aspartic acid proteinase, the reporter peptide is split. Fluoresceine and rhodamine are then too far away to assure an energy transfer. After exposure of the cleavage products to a given wavelength (about 490 nm), only the green fluorescence of the fluoresceine is detectable.

When a substance inhibiting aspartic acid proteinase is discovered, a specificity control test is carried out by incubating this substance in a transcription and translation reaction permitting the expression of another reporter gene (type GFP) to verify that this substance is not in fact a transcription or translation inhibitor.

Each time that a new proteinase inhibitor is discovered, a series of complementary tests are carried out on transcription and translation reactions permitting the expression of proteases resistant to the anti-proteases. Thus, the discovered substance can be rapidly characterized in order to know if it is capable of inhibiting the proteases of the viral strains currently resistant to the anti-proteases.

A representation of the process of the invention is illustrated schematically in FIG. 1.

EXAMPLE VII

High Flow Rate Screening of RecA Intein Proteic Splicing Inhibitor of *Mycobacterium Tuberculosis*

Davis et al., (1992) show that the excision of the RecA intein of *Mycobacterium tuberculosis* is indispensable to the activity of this protein (1). The inteins are recently discovered proteic introns at the interior of proteic sequences. They possess all the information necessary for their proper excision. This recently highlighted process is comparable to the splicing of the RNA premessangers. Thus, by convention, the internal proteic sequence is called intein and the two external sequences, exteins (3). This phenomenon of specific proteic excision is very fast. These inteins were discovered in groups of very different genes and they are at the same time present in both prokaryotes and eukaryotes.

The RecA protein of *Mycobacterium tuberculosis* contains such an element. Other *Mycobacterial* pathogens can possess such a sequence in RecA such as *Mycobacterium Leprae*. Nevertheless, these two proteic introns are different in size, in sequence and in their localization, which makes them very specific.

By inhibiting the proteic splicing of the *Mycobacterium tuberculosis* intein, the activity of the RecA protein is inhibited and therefore the multiplication of this pathogenic organism. In the present case, the inhibition of the splicing represents a new therapeutic pathway against the multiplication of the bacteria responsible for tuberculosis. Only an in vitro test, such as that proposed, permits analysis of the inhibition of a proteic splicing phenomenon, too rapid to be able to be analyzed in vivo.

Figure 2:
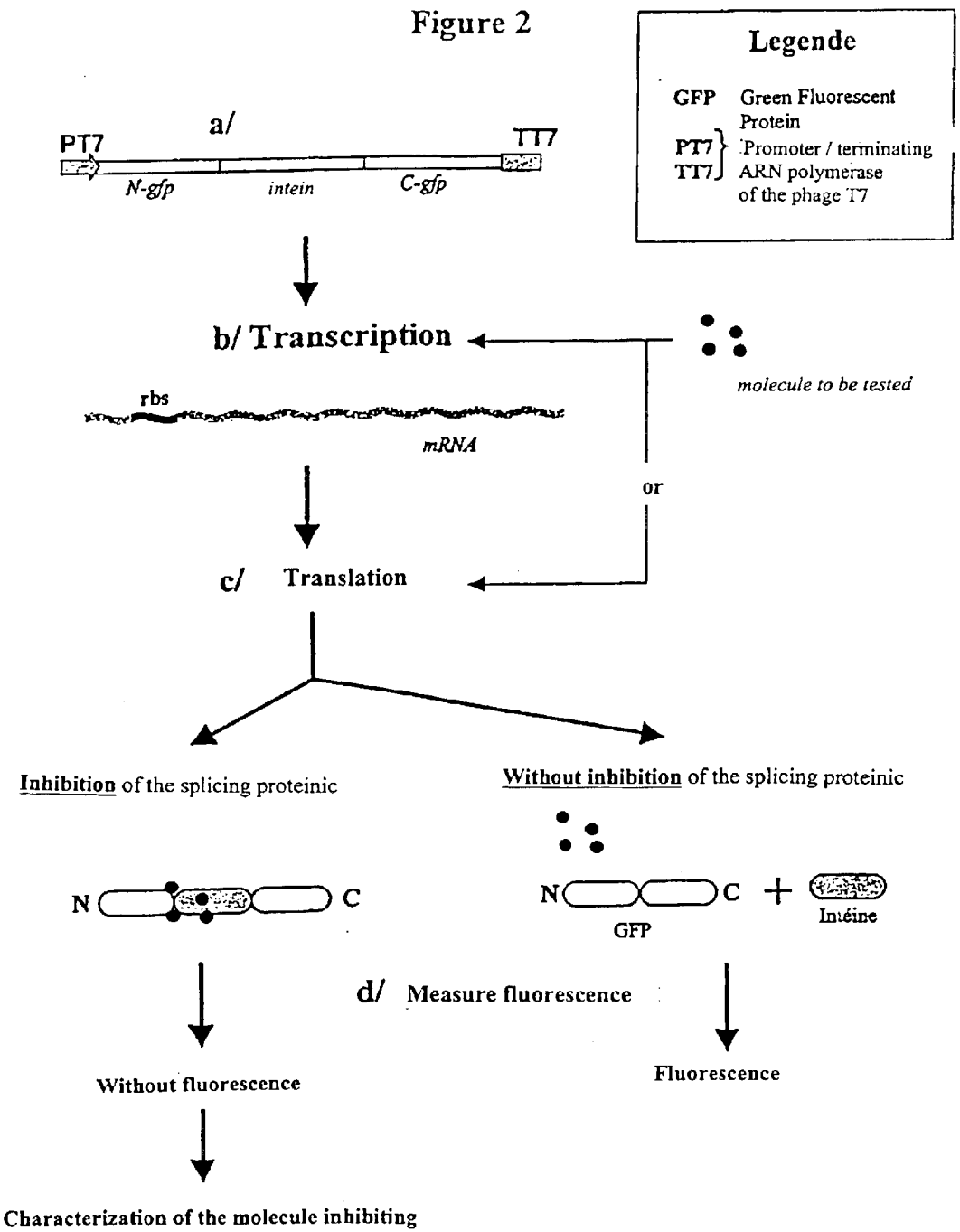
FIG. 2 is a schematic representation demonstrating the process of the invention with the RecA intein proteic splicing inhibitor of *Mycobacterium tuberculosis*.

A screening system for RecA intein splicing inhibitors of *Mycobacterium tuberculosis* has been perfected. The proposed test rests on the process of the invention and consists of expressing in vitro the gene coding for a reporter protein such as GFP, within which the *Mycobacterium tuberculosis* recA gene intein was inserted. Before any expression reaction a substance of pharmacological interest from a bank is added to the transcription and translation mixture. If this substance is active insofar as the inhibitor, it prevents the splicing of the intein after the translation, which inhibits the expression of the mature GFP. To the contrary, if this substance is inactive, the GFP activity can be detected (FIG. 2).

For each substance having an intein splicing inhibitory activity, a second test permits verification that this substance is specific. This second test consists of incubating said substance in the transcription and translation mixture containing the gfp gene without any intein and verifying that the gene can be transcribed and translated in the presence of this substance.

The automation of this screening can be carried out according to the same conditions previously.

The substances thus detected can be tested on other inteins that are of interest in a given process.

EXAMPLE VIII

High Flow Rate Screening of Beta-lactamase Inhibitors

The beta-lactamines (penicillins and cephalosporins) represent the most used class of the antibiotics in anti-infectious therapy. Since the introduction of these molecules in therapy, new resistances to these compounds have developed. Among the different resistance mechanism acquired by the resistant germs, one of the most important consists of producing an enzyme (of the beta-lactamase type) capable of hydrolyzing the antibiotic molecule before if has been able to act. On account of the intensive worldwide use of antibiotics, the speed of the appearance of new resistances is currently faster than the discovery of new antibiotics. On the other hand, there exist few beta-lactamase "suicide" inhibitors (clavulanic acid (in association with amoxicillin in Augmentin), sulbactam and tazobactam) on the market, and already resistances to these new compounds have been demonstrated in hospital environments. The object is therefore to develop a high flow rate screening system to find new beta-lactamase TEM-1 inhibitors.

The screening for new suicide inhibitors consists of carrying out a transcription and translation reaction permitting expression of the TEM-1 beta-lactamase. The gene bla is under the control of T7 phage RNA polymerase promoter and terminator sequences. After this transcription and translation reaction, a substance resulting from a bank of molecules of pharmacological interest is added to the reaction mixture. If this substance is active insofar as a beta-lactamase inhibitor, it inhibits the catalytic activity of the enzyme. In another case, an active beta-lactamase is produced. The beta-lactamase activity is then evaluated by means of a chromogenic substrate of the beta-lactamase: nitrocephine.

The automation of the screening can be carried out according to the same conditions described previously.

When an inhibitor substance has been identified, a series of complementary tests is carried out in order to test the effectiveness of the discovered molecule on the collection of the beta-lactamase mutants known as resistant to the inhibitors. For this, the activity of the different variants of this beta-lactamase expressed in vitro according to the process of the invention is evaluated in the presence of an inhibitor substance, and the activity test of these beta-lactamases is then carried out as described above.

EXAMPLE IX

Comparison of Several Functional Tests Implemented in the Process According to the Invention 1) Comparison of Several Functional Tests The method of the invention permits a comparison of the sensitivity and the reproducibility of several types of functional tests in a very short time. In this experiment, the TEM-1 beta-lactamase was expressed in vitro by using 0.5 μg of mRNA of this gene and by translating this enzyme as described by Zubay in a final volume of 100 μl.

a) Test 1: measurement of the nitrocephine hydrolysis.

Different volumes (5, 10, 15, 20, 15, 30 μl) of this translation mixture were incubated at 37° C. in a final volume of 250 μl of activity revelation buffer (final concentration: NaP 40 mM pH 7.0, 100 μg/ml of nitrocephine and 0.25 mM DMSO). The reaction was followed by spectrophotometry at 486 nm, and the activity values obtained were expressed in obtained maximum activity percentage. These measurements were made in triple specimens in order to evaluate the reproducibility of the revelation technique.

b) Test 2: measurement of the ampicillin hydrolysis by direct revelation

Different volumes (5, 10, 15, 20, 25, 30 μl) of the translation mixture were incubated at 37° C. in a final volume of 250 μl of activity revelation buffer (final concentration: NaP 35 mM pH 7.5, and 160 μg/ml of ampicillin). The reaction was then followed by spectrophotometry at 235 nm, and the activity values obtained were expressed in obtained maximum activity percentage. These measurements were made one triple specimens in order to evaluate the reproducibility of the revelation technique.

c) Test 3: measurement of the ampicillin hydrolysis by fluorescence revelation (Chen K. C., and Holmes K. K., 1986, Enhancement of fluorescence development of end products by use of a fluorescence developer solution in a rapid and sensitive fluorescent spot test for specific detection of microbial beta-lactamases, J. Clin. Microbiol., 23 (3), 539–544).

Different volumes (5, 10, 15, 20, 25, 30 μl) of the translation mixture were incubated at 25° C. for 15 minutes in a final volume of 210 μl of buffer I (final concentration final: 200 μg/ml of ampicillin). 40 μl of revelation buffer II were added (buffer II: sodium tartrate 0.78 M pH 4.5, formaldehyde 12%), and the reaction was incubated 10 minutes at 45° C. The reacting was made by fluorimetry with an excitation wavelength of 430 nm, and the obtained activity values were expressed by percentage of the maximum activity obtained. These measurements were made in triple specimens in order to evaluate the reproducibility of the revelation technique. A control was made without enzyme.

d) Conclusions

FIGS. 4, 5 and 6 illustrate the comparison of the sensitivity and of the reproducibility of several methods of detection of a function.

FIG. 4 indicates that activity test 2 (ampicillin) doe not permit revelation of the enzyme activity whatever its concentration. On the other hand, tests 1 and 3 permit the obtaining of a signal that is correlated to the translation volume added in the test. On the other hand, the activity test 3 (fluorescence) seems to give a less sensitive response than activity test 1 (nitrocephine) for low concentrations of enzyme. But, FIGS. 5 and 6 indicate that test 3 is more reproducible than test 1. Test 3 can therefore be considered as a test of choice for measuring the activity of this beta-lactamase function.

The process of the invention therefore permits testing and validation in very little time of the sensitivity of several methods of detection of a function. This type of application is particularly interesting in the scope of the developing of a system of screening which often requires the most precise and most reproducible sensitivity test possible, in order to be able to detect the variation of a function by this test during the addition of a substance.

2) Molecular screening of substances that can have an activity on a target.

a) Screening of new TEM-1 inhibitors

The β-lactamines (penicillins and cephalosporins) represent the most used class of antibiotics in anti-infectious therapy. Since the introduction of these molecules in therapy, new resistances to these compounds have developed, favoring the expansion of nosocomial infections. Among the different resistance mechanisms acquired by the germs, one of the most important consists of producing an enzyme (TEM-1 β-lactamase for certain enterobacterium for example, or PSE beta-lactamase for *Pseudomonas aeruginosa*) capable of hydrolyzing the antibiotic before it is able to act. There exist some β-lactamase inhibitors used synergistically with an antibiotic, but as they advance new forms of β-lactamases resistant to these inhibitors appear.

A screening of new TEM-1 β-lactamase inhibitors was carried out by the process of the invention. This enzyme was expressed in vitro as described by Zubay by using 300 μg of mRNA in a final translation volume of 5 ml. Each microtitration plaque well was filled with 5 μl of a potential inhibitor solution (of clavulanic acid and sulfactam) such that this inhibitor was at a concentration of 0.4 μM in the final test volume. Then 3 μl of the translation mixture were added in each microtitration plaque well and the mixture was incubated 3 minutes at 25° C. The volume was then completed to 58 μl with a revelation solution (final concentration: NaP 40 mM pH 7.0, 100 μg/ml of nitrocephine and 0.25 mM DNSO). The reaction was followed by spectrophotometry at 486 nm. Three controls were carried out: one without translation extract (therefore without enzyme), one with the substrate alone, and one without any potential inhibitor.

It appears on FIG. 7 that only the substance that was added in the well E2 inhibited the activity of the TEM-1 beta-lactamase.

By measuring the residual activity of the well E2 and by comparing it to the control without inhibitor, it appears that this potential inhibitor #1 (that is in fact clavulanic acid) reduces by 52% the TEM-1 activity.

A similar experiment was carried out with a final potential inhibitor concentration of 21.5 μM. It then appears from FIG. 8 that the potential inhibitor #1 is still active, and that a new potential inhibitor #2 is revealed in well B12. A measurement of the residual activity in wells E2 and B12 indicates that the inhibitor #1 at 21.5 μM reduces the TEM-1 activity by 80%, against 73% for the inhibitor #2 (which is in fact sulbactam).

After this first type of screening, it is contemplated to characterize the potential inhibitor(s) on equivalent targets (other beta-lactamases for example) or on mutants of the initial target (mutants of the TEM-1 beta-lactamase resistant to the beta-lactamase inhibitors).

This characterization was carried out by the potential inhibitor #1 (the most effective according to the previous experiments) on two TEM-1 beta-lactamase mutants described as being resistant to a beta-lactamase inhibitor. For this 5 µl of a translation mixture expressing either the native enzyme or one of the two mutants were separately incubated at 25° C. for 3 minutes in a final volume of 500 µl of buffer I (final concentration: NaP 50 mM pH 7.0, 1.5 µM potential inhibitor #1). Then 100 µg/ml of nitrocephine and 0.25 mM final of DMSO were added, and the reaction was followed by spectrophotometry at 486 nm. The obtained results were expressed in maximum activity percentage measured on the enzyme in the absence of inhibitor.

FIG. 9 indicates that under these conditions, the native TEM-1 enzyme is 87% inhibited, whereas the two mutants retain respectively a 26% and 35%. If the inhibitor #1 seems effective against the native enzyme, it appears that it is not against enzymes that are already resistant to a beta-lactamase inhibitor.

This experiment can be carried out with any other type of target (HIV virus protease, receptors, etc . . . ). The process of the invention therefore permits very rapid implementation of a screening at the molecular level of substances capable of modifying the activity of a target, then validating the results on equivalent targets.

b) Screening of new HIV-1 virus protease inhibitors

A screening of new HIV-1 virus protease inhibitors was carried out by the process of the invention. This enzyme was expressed in vitro as described by Zubay by using 150 µg of mRNA in a final translation volume of 1 ml. Each microtitration plaque well was filled with 60 µl of a mixture containing 10 µl of translation mixture, 30 µl of buffer (2M NaCl, 12 mM EDTA, 200 mM sodium acetate, 2 mM DTT and 20% DMSO), 1 µl at 600 µM of the substrate peptide BACHEM M1865 (peptide DABCYL-Abu-Ser-Gln-Asn-Tyr-Pro-Ile-Val-Gln-EDANS) SEQ ID NO: 1 and 2.5 µM final of different potential inhibitors. This FRET peptide has the property of liberating some fluorescence when it is split by the HIV virus protease. One substance which does not inhibit the activity of the HIV protease is therefore characterized by the appearance of a fluorescent signal when the well is exposed to UV. Three controls were carried out: one without translation extract (therefore without enzyme), one with the substrate alone, and one without any potential inhibitor.

As it appears from FIG. 10, only the substance that was added in the well E8 (pepstatin A) inhibited the HIV protease activity.

The process of the invention therefore permits very simply carrying out an in vitro screening of substances capable of modifying the activity of a function.

These experiments can be carried out with any other type of target (HIV virus protease, receptors, etc). The process of the invention therefore permits very rapid implementation of a screening at the molecular level of substances capable of modifying the activity of a target, then validating the results on equivalent targets.

Bibliographic References

1. Davis E. O., Jenner, P. J., Brooks, P. C., Colston, M. J., Sedgwick, S. G. (1992). Protein splicing in the maturation of *M. Tuberculosis* RecA protein. A mechanism for tolerating a novel class of intervening sequence. *Cell*, 71, 201–210.
2. Davis E. O., Thangaraj, H. S., Brooks, P. C., and Colston, M. J. (1994). Evidence of selection for protein introns in the recAs of pathogenic mycobacteria. *EMBO J.*, 13 (4), 699–703.
3. Perler F. B., Davis E. O., Dean, G. E., Gimble, F. S., Jack, W. E., Neff, N., Noren, C. J., Thorner, J., and Belfort, M. (1994). Protein splicing elements: inteins and exteins—a definition of terms and recommended nomenlclaure. *Nucl. Acids Research*, 22, 1125–1127.
4. Vasudevachari, M. B., Zhang, Y. M., Imamichi, H., Imamichi, T., Falloon, J., and Salzman, N. P. (1996). Emergence of protease inhibitor resistance mutations in human immunodeficiency virus type 1 isolates from patients and rapid screening procedure for their detection. *Antimicrob Agents Chemother*, 40 (11), 2535–2541.
5. Chen, K. C. and Holmes K. K. (1986). Enhancement of fluorescence development of end products by use of a fluorescence developer solution in a rapid and sensitive fluoresecent spot test for specific detection of microbial beta-lactamases, *J. Clin. Microbiol.*, 23(3), 539–544.
6. Gurevich, V. A., Pokrovskaya I. D., Obukhova T. A., and Zozulya S. (1991). Preparative in vitro mRNA synthesis using SP6 and T7 polymerases, Anal. Biochem., 195, 207–213.
7. Zubay G. (1973). In vitro synthesis of protein in microbial systems, Ann. Rev. Genet., 7, 267–287.

---

---

What is claimed is:

1. A method of screening a substance able to modify the known function of one or more proteins comprising the steps of:
   (a) producing in vitro said proteins
   (b) measuring and/or detecting variation of the known function in the presence and in the absence of the substance which is screened.

2. The method of claim 1, further comprising the following steps:

a) preparing at least one nucleic acid molecule comprising the gene(s) coding for one or several proteins and the control elements necessary for the transcription and the translation of said gene(s), b) transcribing the nucleic acid molecule(s) prepared at step (a), c) translating in vitro the transcript(s) prepared at step (b), d) detecting and/or measuring the variation of a known function corresponding to the proteins produced at step (c) in the presence and in the absence of said substance or to the substance in the presence and in the absence of the proteins produced at step (c).

3. The method of claim 2, wherein preparation of one or several nucleic acid molecules of step (a) consists of placing the gene(s) coding for said protein(s) under the control: of a 5' promoter for transcription and/or of a ribosome binding site upstream of said gene(s) for translation.

4. The method of claim 3, comprising detecting and/or measuring variation of the known function of the protein(s) produced at step (c).

5. The method of claim 4, wherein step (a) comprises preparation of the nucleic acid molecule(s) by amplifying the gene(s) coding for said protein(s).

6. The method of claim 5, wherein step (a) comprises preparing the nucleic acid molecule(s) by PCR or NASBA type amplifying of the gene(s) coding for said protein(s), with the aid of one or several pairs of primers, each one comprising:

(a) some sequence hybridizing upstream of one or several nucleic acid molecules comprising gene(s) coding for said protein(s), and of an RNA polymerase promoter for the sense primer, and (b) some sequence hybridizing downstream of one or several nucleic acid molecules comprising gene(s) coding for said protein(s) for the antisense primer.

7. The method of claim 2, wherein after step (d), it is verified that said substance does not inhibit one of steps (a) to (c).

8. A kit for the implementation of the method of claim 2, wherein said kit comprises: means for revealing the function, an RNA polymerase, nucleotide sequences for the preparation of the nucleic acid molecules comprising the gene(s) permitting the expression of protein(s) corresponding to the detected and/or quantified function, four triphosphate nucleotides, and mixtures necessary for said preparation, transcription and translation steps.

9. The kit of claim 8, wherein said kit further comprises:

(a) products necessary for the preparation of the nucleic acid molecules comprising the gene(s) permitting the expression of the protein(s) corresponding to the detected and/or quantified function, and/or (b) a support containing: means for revealing a function, an RNA polymerase, four triphosphate nucleotides, and mixtures necessary for said transcription and translation steps.

10. The method of claim 6, wherein, for the sense primer, the sequence hybridizing upstream of one or several nucleic acid molecules further comprises genes coding for a ribosome binding site.

11. The method of claim 6, wherein, for the antisense primer, the sequence hybridizing downstream of one or several nucleic acid molecules further comprises genes coding for an RNA polymerase terminator.

12. The method of claim 4, wherein said function corresponds to a collection of target proteins of which the genes coding for these proteins are located on the same DNA fragment as in the case of an operon, or at different places of the DNA.

13. The method of claim 12, wherein step (a) comprises preparing a nucleic acid molecule comprising genes (the operon) coding for the proteins, 5' of the collection of said genes (from the operon) a DNA polymerase promoter, and for each of said genes its natural ribosome binding site.

14. The method of claim 13, wherein the ribosome binding site of each one of the genes is its natural ribosome binding site and, at step (c), a translation extract is prepared starting from the organism that the target gene(s) come from.

15. The method of claim 12, wherein step (a) comprises preparing one or several nucleic acid molecules comprising the genes coding for the proteins, 5' of each of said genes an RNA polymerase promoter and a ribosome binding site.

16. The method of claim 15, wherein the ribosome binding site is the natural site of each one of the genes.

17. The method of claim 1, wherein said proteins are different mutants of a protein or different mutants of a collection of proteins.

18. The method of claim 2, wherein one of several reporter molecules are added at one of steps (a), (b), (c) or (d) permitting detecting and/or measuring of the activity of the protein(s) produced at step (c) or of the substance.

19. The method of claim 2, wherein the reporter molecule is a molecule capable of directly or indirectly revealing the activity of one or several of said proteins or of said substance.

20. The method of claim 19, wherein the reporter molecule is a protein that is produced during step (c) conjointly with said protein(s).

21. The method of claim 20, wherein the gene coding for the reporter molecule is placed under the control of transcription and translation regulation sequences corresponding to those of the gene(s) coding for said protein(s), such that the reporter gene is co-expressed with said gene(s).

22. The method of claim 18, wherein said protein or one of said proteins produced at step (c) is also a reporter molecule.

23. The method of claim 2, further comprising introducing said substance before, after and/or during the transcription and/or translation of steps (b) and/or (c) and/or of detecting and/or of measuring of the variation of at least one known functional step (d).

24. The method of claim 1 wherein, said substance comprises polynucleotides, peptides, proteins, ions, molecules or natural or synthetic chemical compositions, hormones, aromatic compounds, antibodies, antibody fragments, genes, cellular receptors, amino acids, glycopeptides, lipids, glycolipids, sugars, polysaccharides, antiviruses, inhibitors, or stimulants.

* * * * *